United States Patent [19]

Inoue et al.

[11] Patent Number: 5,334,188
[45] Date of Patent: Aug. 2, 1994

[54] CONNECTOR WITH INJECTION SITE

[75] Inventors: Yoshifumi Inoue, Ikeda; Hiroshi Yoshioka, Takatsuki, both of Japan

[73] Assignee: Nissho Corporation, Osaka, Japan

[21] Appl. No.: 990,932

[22] Filed: Dec. 14, 1992

Related U.S. Application Data

[60] Continuation of Ser. No. 714,991, Jun. 14, 1991, abandoned, which is a continuation of Ser. No. 453,882, Dec. 20, 1989, abandoned, which is a division of Ser. No. 275,306, Nov. 23, 1988, abandoned.

[30] Foreign Application Priority Data

Dec. 7, 1987 [JP] Japan ................... 62-186267
Dec. 7, 1987 [JP] Japan ................... 62-308860

[51] Int. Cl.⁵ ............................................. A61M 5/31
[52] U.S. Cl. ................................. 604/283; 604/244; 604/905; 604/256; 285/3
[58] Field of Search ............... 604/83, 86, 88, 91, 604/165, 167, 206, 244, 256, 283, 284, 415, 905; 275/247; 251/149.1, 149.4; 285/3, 331, 386

[56] References Cited

U.S. PATENT DOCUMENTS

| | | |
|---|---|---|
| 1,687,324 | 2/1925 | Cook . |
| 2,531,893 | 10/1947 | Roehr . |
| 3,202,442 | 8/1965 | Abbey et al. ............... 285/3 |
| 3,391,951 | 7/1968 | Miller ....................... 285/3 |
| 3,502,097 | 3/1970 | Muller ...................... 604/86 |
| 3,739,779 | 6/1973 | Pfleger ..................... 604/205 |
| 3,986,508 | 10/1976 | Barrington ................. 285/3 |
| 4,019,512 | 4/1977 | Tenczar .................... 285/3 |
| 4,170,993 | 10/1979 | Alvarez .................... 604/263 |
| 4,254,773 | 3/1981 | Waldbillig . |
| 4,508,367 | 4/1985 | Oreopoulos et al. ....... 285/3 |
| 4,512,766 | 4/1985 | Vailancourt . |
| 4,559,043 | 12/1985 | Whitehouse et al. . |
| 4,578,063 | 3/1986 | Inman et al. ............... 604/244 |
| 4,629,455 | 12/1986 | Kanno . |
| 4,636,204 | 1/1987 | Christopherson et al. ... 604/905 |
| 4,673,400 | 6/1987 | Martin . |
| 4,752,292 | 6/1988 | Lopez et al. . |

FOREIGN PATENT DOCUMENTS

| | | |
|---|---|---|
| 1105959 | 1/1979 | Canada ...................... 604/905 |
| 1114677 | 8/1984 | European Pat. Off. . |
| 0157224 | 10/1985 | European Pat. Off. ..... 604/283 |
| 2720470 | 11/1977 | Fed. Rep. of Germany . |
| 2322614 | 4/1977 | France . |
| 2486803 | 1/1982 | France . |

*Primary Examiner*—Ralph Lewis
*Attorney, Agent, or Firm*—Armstrong, Westerman, Hattori, McLeland & Naughton

[57] ABSTRACT

A connector assembly including an injection needle for providing fluid communication through a closed injection site at one end of an infusion line for infusing fluid therapy to a patient which includes an injection needle, a hub at one end of the needle, a tube connected to the hub, and a connector mounted to the hub. The connector includes a thread or other device for securing the connector to a complimentary connector provided the end of the infusion line. A second end of the needle extends beyond the thread or other device to permit the needle to pierce the injection site prior to engagement of the thread or other device with the complimentary connector and at least one of the two connectors is mounted for rotary movement relative to the needle and the injection site to permit the connectors to be secured together by rotary movement subsequent to piercing the needle through the injection site without rotating the needle. The connector is preferably mounted for rotary movement relative to the hub and a thread is provided on an external or internal surface of the connector.

6 Claims, 6 Drawing Sheets

CONNECTOR WITH INJECTION SITE

This application is a continuation of application Ser. No. 07/714,991 filed Jun. 14, 1991, now abandoned which application is a continuation of Ser. No. 453,882, filed Dec. 20, 1989, now abandoned which application is a division of application Ser. No, 275,306, filed Nov. 23, 1988, now abandoned.

BACKGROUND OF THE INVENTION

The present invention relates to a connector with an injection site and applications thereof, and more particularly to a connector with an injection site and applications thereof capable of, when infusing other liquid drug or nutrient fluid together with liquid drug or nutrient fluid to be infused during fluid therapy such as total parenteral nutrition or intravenous hyper alimentation, infusing liquid drug and/or nutrient fluid (hereafter referred to as liquid drug and the like) from another infusion line through an injection site by providing the injection site at a midway of the infusion line; and capable of, when infusing plural kinds of liquid drug and the like using the same intravenous catheter, infusing plural kinds of liquid drug and the like in order through an injection site by providing the injection site at a proximal portion of the intravenous catheter, i.e. at an introducing portion of liquid drug and the like.

When infusing some liquid drug and the like together with other liquid drug and the like to be infused during fluid therapy such as total parenteral nutrition, there are usually used a solution infusion set or catheter (hereafter referred to as infusion tube) having a part called "injection site" at a midway of the infusion route. The other liquid drug and the like can be infused by sticking a needle of other infusion line into a rubber plug in the injection site of the infusion tube and by making the infusion tube communicate with the other infusion line.

In the fluid therapy using an infusion line comprising an infusion tube and an intravenous catheter connected to the infusion tube, the solution infusion is sometimes interrupted for a long period of time. In that case, the infusion tube is detached from the intravenous catheter and a cap with a rubber plug called "injection plug" is put on the proximal portion of the intravenous catheter (a portion to be connected to the infusion tube). When the temporal solution infusion is required during interruption of a solution infusion, a needle of other infusion line is sticked into the rubber plug of the injection plug to make the intravenous catheter communicate with the other infusion line and to infuse solution.

In the conventional infusion line using an injection site or an injection plug, however, a needle sometimes pulls out from the rubber plug when a patient under fluid therapy moves or touches the infusion line, since the needle is merely sticked into the rubber plug in the injection site or injection plug. Further there is a danger of infection from the air since a part of the needle is exposed to the air.

The present invention was made to solve the above-mentioned problems, and it is an object of the present invention to provide a connector with an injection site which can prevent the pulling out of a needle of the other infusion line during fluid therapy, isolate the needle from the air to prevent the invasion of bacteria from the injection site.

SUMMARY OF THE INVENTION

In accordance with the present invention, there is provided a connector with an injection site comprising a tubular body having one or more fluid inlet and a fluid outlet, wherein a cap or plug made of rubber-like elastic material is fit into at least one fluid inlet to form an injection site, and a connecting means is provided on the external wall of the injection site or on the external wall of the tubular body near the injection site.

The connector with an injection site of the present invention has a connecting means on the external wall of the injection site or on the external wall of the tubular body near the injection site. Accordingly, when a needle of a device to be connected to the connector, for example, the needle of an infusion line having on the side of the needle a connecting means corresponding to the connecting means of the connector with the injection site is sticked into, for example, a rubber plug of the injection site of the connector, and the connecting means of the connector and that of the infusion line is connected to each other, the firm connection can be obtained.

Further when the connecting means of the connector and that of the infusion line are so designed as to provide an airtight connection, infection from the air can be certainly prevented since the needle of the infusion line is isolated from the air and the needle is not pulled out from the rubber plug of the injection site during the use of infusion line.

BRIEF EXPLANATION OF THE DRAWINGS

FIG. 2b is a partially explanatory view showing a connection end of an infusion line to be connected to the connector shown in FIG. 2a;

FIGS. 3b, 4b and 5b are respectively partially sectional views showing connection ends of infusion lines to be connected to the connectors shown in FIGS. 3a, 4a and 5a;

FIG. 7b is a partially longitudinal sectional view of an infusion tube to be connected to the injection needle of FIG. 7a;

DETAILED DESCRIPTION OF THE INVENTION

Referring now to the accompanying drawings a connector of the present invention is explained.

Figure 1:
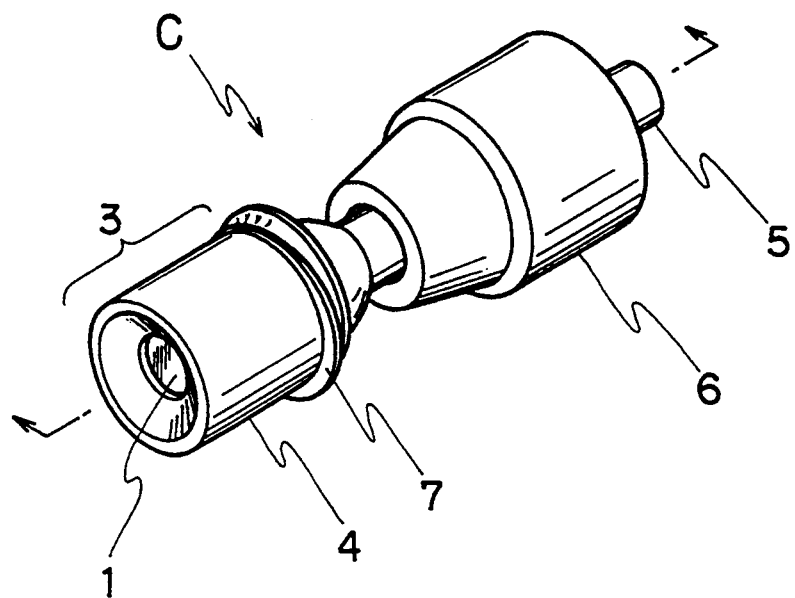
FIG. 1 is a perspective view of an embodiment of a connector of the present invention.

FIG. 1 is a perspective view of an embodiment of a connector of the present invention. The connector of FIG. 1 has a male screw as a connecting means and a connecting means comprising a female screw is provided at a fluid outlet.

Figure 2A:
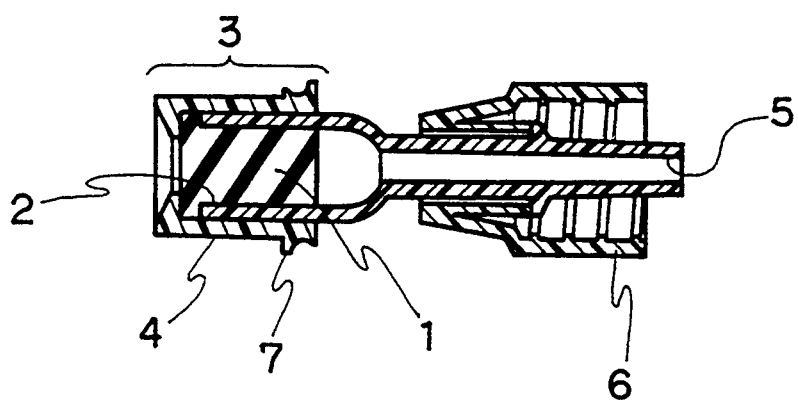
FIG. 2a is a sectional view taken along the line X—X of FIG. 1.
Figure 3A:
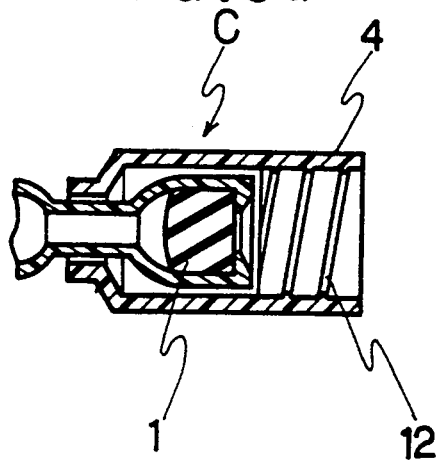
FIGS. 3a, 4a and 5a are partially sectional views of other embodiments of a connector of the present invention.
Figure 3B:
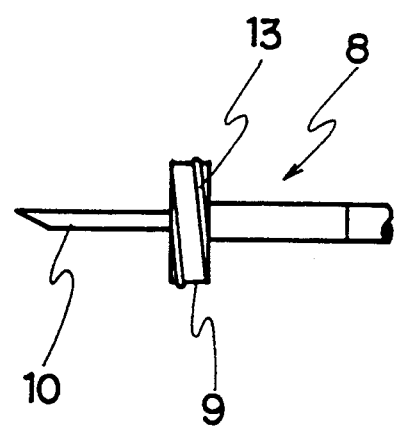
Figure 4A:
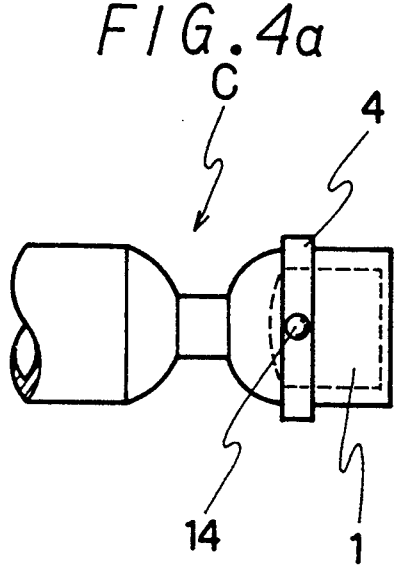
Figure 4B:
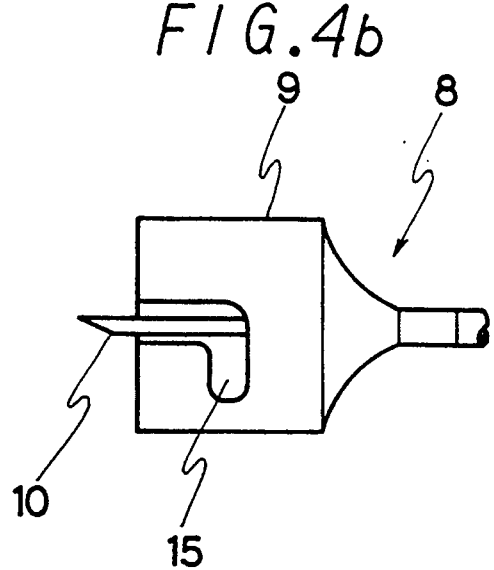
Figure 5A:
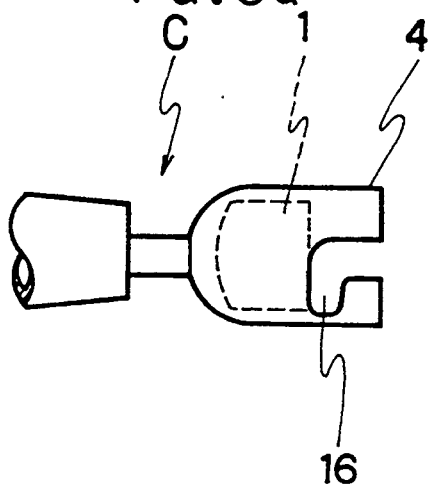
Figure 5B:
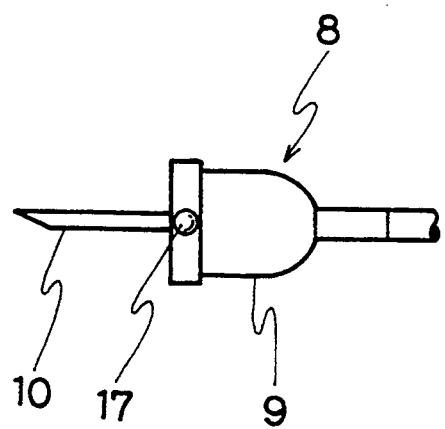

FIG. 2a is a sectional view taken along the line X—X of FIG. 1. FIGS. 3a, 4a and 5a are partially sectional views of other embodiments of a connector of the present invention, and FIGS. 3b, 4b and 5b are respectively partially sectional views showing connection ends of infusion lines to be connected to the connectors shown in FIGS. 3a, 4a and 5a.

As shown in FIGS. 1, 2a, 3a, 4a and 5a, a connector C of the present invention is a tubular connector having an injection site 3, and characterized in that a connecting means is provided on the external wall of the injection site 3 or on the external wall of the tubular body near the injection site 3. The connector C can be airtightly connected to an infusion line 8 having at its connection end a connecting means 9 of which shape corresponds to that of the connecting means 4 of FIG. 2a, FIG. 3a, FIG. 4a or FIG. 5a, as shown in FIGS. 2b, 3b, 4b and 5b. That is, the connector C and the infusion line 8 can be airtightly and firmly connected to each other by sticking a needle 10 of the infusion line 8 into the injection site 3 of the connector to make the connector C communicate with the infusion line 8 and then by combining both connecting means.

The connector of the present invention is hereinafter explained in detail mainly based on FIGS. 1 and 2a.

The injection site 3 is used for infusing plural kinds of liquid drug into a patient by adding other liquid drugs from other infusion lines during fluid therapy. The injection site 3 comprises a tubular body (a part of the connector C excepting connecting means 4 and 6) having one or more fluid inlet 2 and a fluid outlet 5. A cap or plug made of rubber-like elastic material is liquid-tightly put on at least one fluid inlet 2. In the case of a cap, it is put on the fluid inlet 2, while in the case of a plug, it is inserted into the fluid inlet 2 as shown in FIG. 2a. In that case, a means for supporting the cap or rubber plug 1 might be provided to prevent the detachment of the cap or rubber plug 1. In FIG. 2a, the connecting means 4 comprises a tubular portion functioning as a supporting means, and a male screw 7.

As described above the cap or plug is made of rubber-like elastic material. Concrete examples of the rubber-like elastic material are, for instance, natural rubber and synthetic rubber such as butadiene rubber, styrene-butadiene rubber, isoprene rubber, ethylenepropylene rubber, butyl rubber, chloroprene rubber, nitrile rubber, acrylic rubber, urethane rubber and silicone rubber. Among them, in particular, natural rubber, isoprene rubber, chloroprene rubber and silicone rubber are preferably used since they have small sticking resistance and good sealing property.

The connecting means 4 on the side of the fluid inlet 2 serves to connect the connector C to a device having a needle at its one end (hereafter representatively referred to as infusion line). The connecting means 4 alone does not function as a connector, but it cooperates with a connecting means 9 formed at the connecting end of the infusion line 8 and combines the connector with the infusion line. Accordingly the shape of the connecting means 9 at the connection end of the infusion line 8 varies depending on the shape of the connecting means 4. That is, the shape of the connecting means 4 of the connector C and that of the connecting means 9 of the infusion line 8 are supplementary to each other. Such relationship is found in, for example, a male screw 7 in FIG. 2a and a female screw 11 in FIG. 2b; a female screw 12 in FIG. 3a and a male screw 13 in FIG. 3b; a projection 14 in FIG. 4a and a slit 15 in FIG. 4b; and a slit 16 in FIG. 5a and a projection 17 in FIG. 5b. The connecting means 4 might be composed solely of a male screw or a female screw, or might be composed of a tubular portion, and a male screw or a female screw as shown in FIGS. 2a and 3a.

The connecting means 4 is provided on the external wall of the injection site 3 or on the external wall of a tubular portion near the injection site 3. When the connector C and the infusion line 8 is connected to each other after a needle 10 of the infusion line 8 is sticked into the plug 1 of the injection site 3, it is preferable that the connecting means 4 is so provided as to prevent the rotation of the needle in the rubber plug 1. Concretely speaking, the male screw 7 is preferably fixed to the connector C, i.e. adhered to or formed integrally with the connector C, when the connecting means 4 comprises the male screw 7 (see FIG. 2a). When the connecting means 4 comprises the female screw 12, it is preferable that the female screw 12 is rotatably provided at the connector C (see FIG. 3a). Further, when the connecting means 4 comprises a projection 14 or a slit 16, the projection 14 or slit 16 might be fixedly or rotatably provided at the connector (see FIGS. 4a and 5a). In that case, it is necessary to employ, as a connecting means 9 of an infusion line 8, a rotatable female screw 11 for a fixed male screw 7; a fixed male screw 13 for a rotatable female screw 12; a rotatable slit 15 or projection 17 for a fixed projection 14 or slit 16; a fixed slit 15 or projection 17 for a rotatable projection 14 or slit 16 (see FIGS. 2b, 3b, 4b and 5b).

A connecting means 6 on the side of the fluid outlet 5 is optionally employed, and therefore is not always necessary. The opening end of a tube might be directly inserted into the fluid outlet 5 and, if necessary, adhered thereto by means of adhesives and the like. In the case where the tube cannot be firmly connected to the connector C for reason of material, however, it is necessary to provide a connecting means 6 at the fluid outlet 5. By means of the connecting means 6, a tube having at its connection end a supplemental connecting means with the connecting means 6, for example, an intravenous catheter can be surely and securely connected to the connector.

As a material for a tubular portion of the connector C, it is preferable to employ synthetic resin having a resistance to liquid drug used as a solution for infusion. There can be preferably used, for example, polyethylene, polypropylene, hard vinyl chloride resin, acrylonitrile-butadiene-styrene copolymer, or styrene-acrylonitrile copolymer. Material for the connecting means 4 and 6 is not particularly limited in the present invention. Synthetic resin is generally employable, and polystyrene, polyamide, polyester, polycarbonate and polymethyl methacrylate can be preferably employed besides the materials described above as a material for the tubular portion of the connector.

Next a method of using a connector C of the present invention is explained.

Figure 2B:
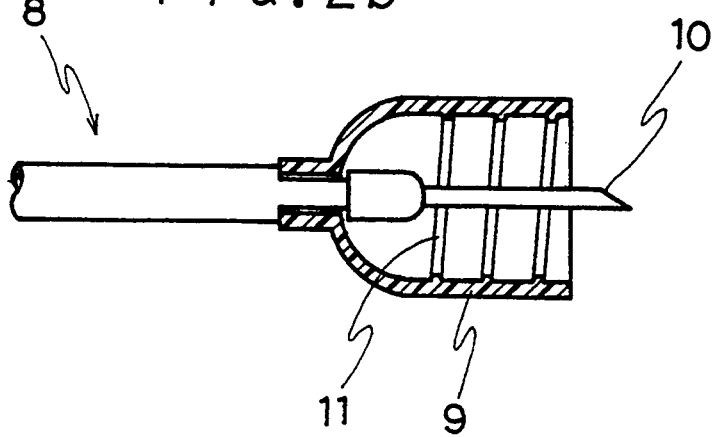

In the case of a connector C shown in FIG. 2a having a male screw 7 as a connecting means 4, a needle 10 of the infusion line 8 having a female screw 11 as a connecting means as shown in FIG. 2b is sticked into a rubber plug 1 of an injection site 3 of the connector C. Then the rotation of the connecting means 9 of the infusion line 8 with one hand in the direction in which the connecting means 9 is screwed, while holding the connector C with other hand, gives the firm connection between the infusion line 8 and the connector C without causing the rotation of the needle 10 in the rubber plug 1.

In the case of a connector C having a projection 14 as a connecting means 4 as shown in FIG. 4a, a needle 10 of the infusion line 8 having a slit 15 as a connecting means as shown in FIG. 4b is sticked into a rubber plug 1 of an injection site 3 of the connector C. Then the rotation of the connecting means 9 of the infusion line 8 with one hand and the insertion of the projection into the slit 15, while holding the connector C with other hand, gives the firm connection between the infusion line 8 and the connector C.

Explanations for the combination of a connector C of FIG. 3a and an infusion line of FIG. 3b, and the combination of a connector C of FIG. 5a and an infusion line of FIG. 5b are omitted since they correspond respectively to those for the combination of a connector C of FIG. 2a and an infusion line of FIG. 2b, and the combination of a connector C of FIG. 4a and an infusion line of FIG. 4b.

Next there are explained in order three embodiments of an injection needle, an intravenous catheter, and an infusion tube which all adapt a connector of the present invention or its conception.

Figure 6:
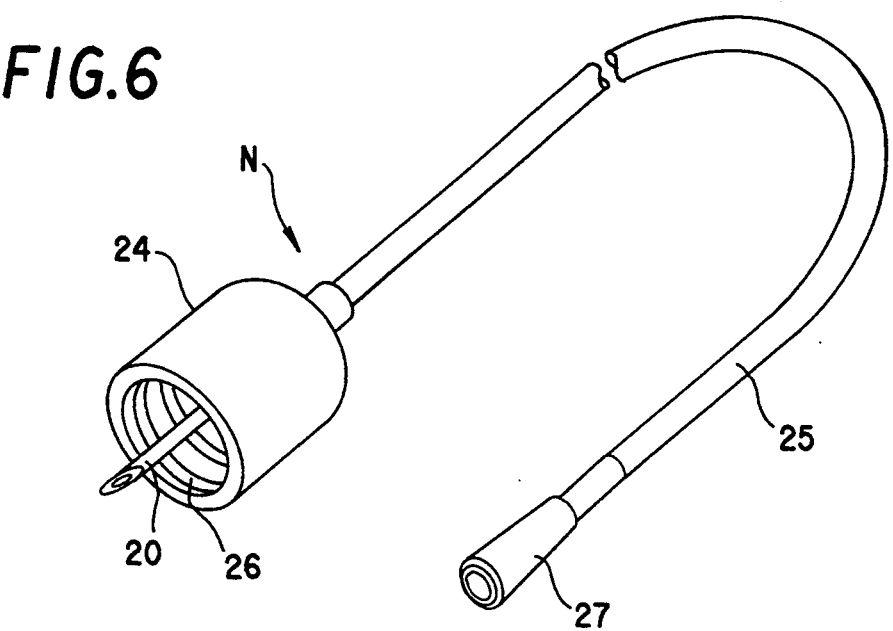
FIG. 6 is a perspective view of an embodiment of an injection needle of the present invention.
Figure 7A:
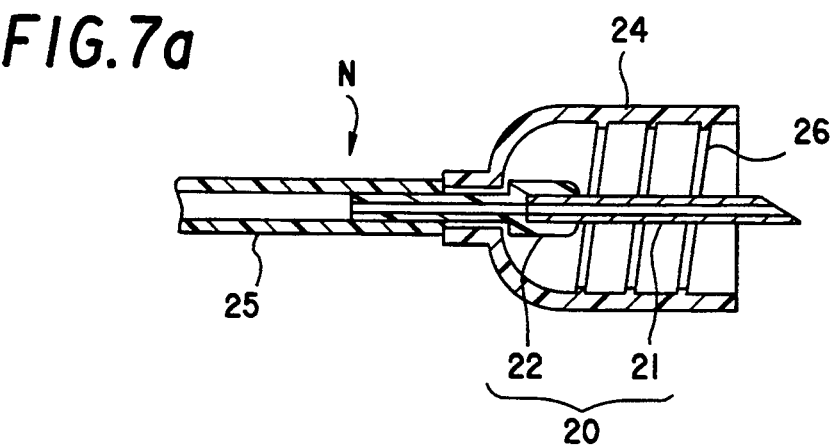
FIG. 7a is a partially longitudinal sectional view of the injection needle of FIG. 6.
Figure 7B:
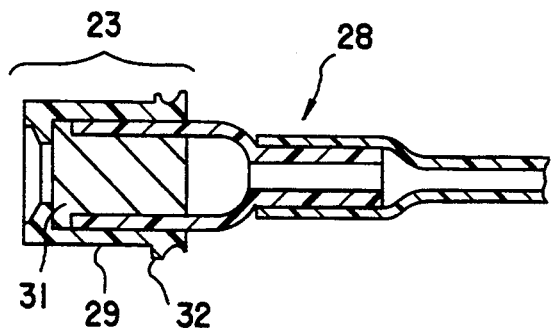

FIG. 6 is a perspective view of an embodiment of an injection needle of the present invention having a female screw as a connecting means. FIG. 7a is a partially longitudinal sectional view of the injection needle of FIG. 6, and FIG. 7b is a partially longitudinal sectional view of an infusion tube to be connected to the injection needle of FIG. 6.

As shown in FIGS. 6 and 7a, an injection needle N of the present invention is characterized in that, in an injection needle having a tube 25 connected to the free end of a hub 22, a connecting means is provided at the hub 22. The injection needle N can be airtightly connected to an infusion tube 28 having, on the outer wall of an injection site 23 or on the external wall of the tubular body near the injection site 23, an connecting means 29 shown in FIG. 7b of which shape corresponds to that of the connecting means 24 of FIG. 7a. That is, the infusion needle N and the infusion tube can be airtightly and securely connected to each other by sticking a needle 20 of the injection needle N into a rubber plug 31 of the injection site 23 of the infusion tube 28 to make the injection needle N communicate with the infusion tube 28 and then by combining both connecting means.

The needle 20 comprises a canula 21 and a hub 22. In use, the needle 20 is sticked into the rubber plug 31 of the infusion tube 28 having an injection site 23 at its connection end and serves to make the injection needle N communicate with the infusion tube 28.

Material for the canula 21 and hub 22, and method of adhering them to each other to fabricate a needle 20 are not particularly limited in the present invention. Conventional material and method can be employed.

A tube 25 is generally made of soft synthetic resin such as soft vinyl chloride resin and polyethylene. The tube 25 is connected to a free end (an end opposite the canula 21) of the hub 22 directly or through other suitable connecting means. The other end of the tube 25 is formed into suitable shapes depending on the purpose or condition of use. That is, a connecting means might be provided at the other end of the tube 25, or the other end might be formed to provide an infusion line. In FIG. 6, a connector 27 for connecting an infusion line and the like is provided at the other end of the tube 25.

The connecting means 24 is provided at the hub 22. It is preferable that the connecting means 24 is so provided as to prevent the rotation of the needle 20 in the rubber plug 31 when the injection needle N is combined with the infusion tube 28 after the needle 20 is sticked into the rubber plug 31 of the injection site 23 of the infusion tube 28. For example, when employing a female screw 26 as a connecting means 24, it is preferable that the female screw 26 is rotatably provided at the hub 22 (see FIG. 7a). In that case, it is necessary to employ a male screw 12 as a complimentary connecting means 29 of the infusion tube 28 for the rotatable female screw 26 (see FIG. 7b).

As a material for the connecting means 24, 29 and rubber plug 31, the same material as in the connecting means and rubber plug of the connector described above can be employed.

A method of using an injection needle N of the present invention is explained.

In the case of an injection needle N shown in FIG. 7a having a female screw 26 as a connecting means 24, a needle 20 of the injection needle N is sticked into a rubber plug 31 of the injection site 23 of the infusion tube 28 having a male screw 32 as a connecting means 29 as shown in FIG. 7b. Then the rotation of the connecting means 24 of the injection needle N with one hand in the direction in which the connecting means 24 is screwed, while holding the infusion tube 28 with other hand, gives the firm connection between the injection needle N and the infusion tube 28.

Next an intravenous catheter adapting a connector of the present invention is explained.

Figure 8:
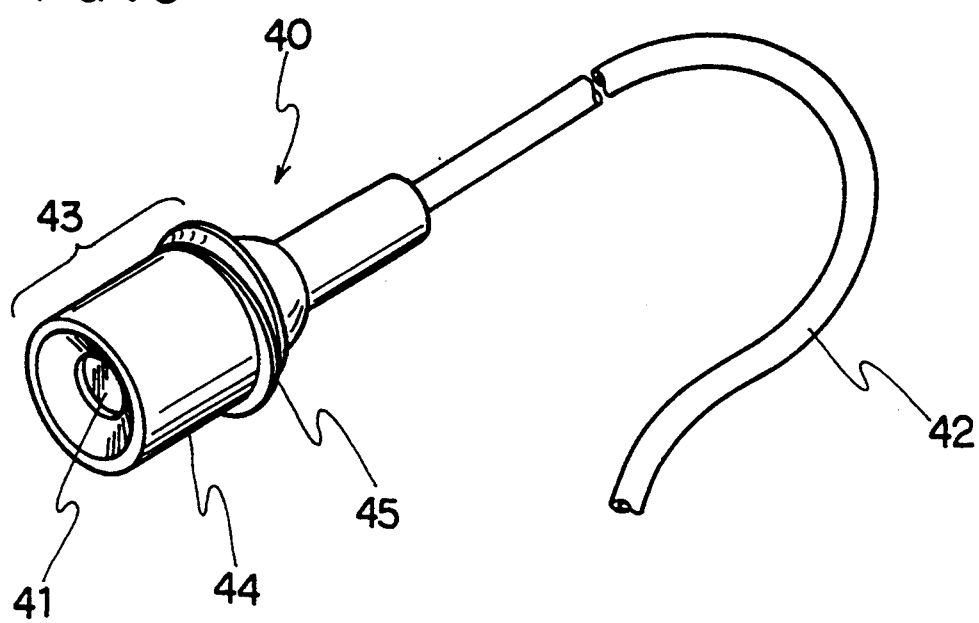
FIG. 8 is a perspective view of an embodiment of an intravenous catheter of the present invention.
Figure 9A:
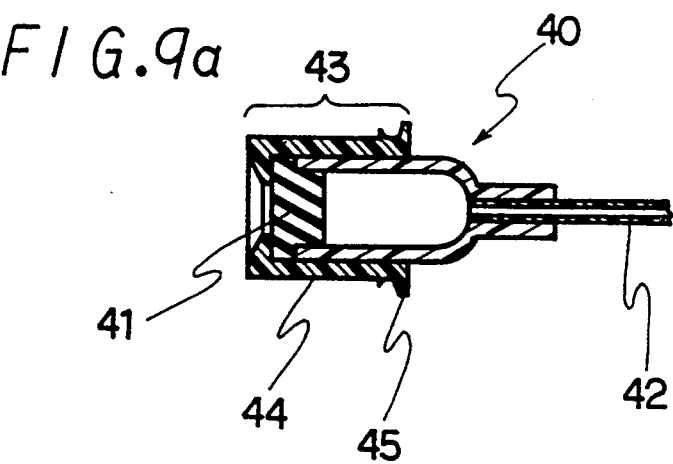
FIG. 9a is a partially longitudinal sectional view of the intravenous catheter of FIG. 8.
Figure 9B:
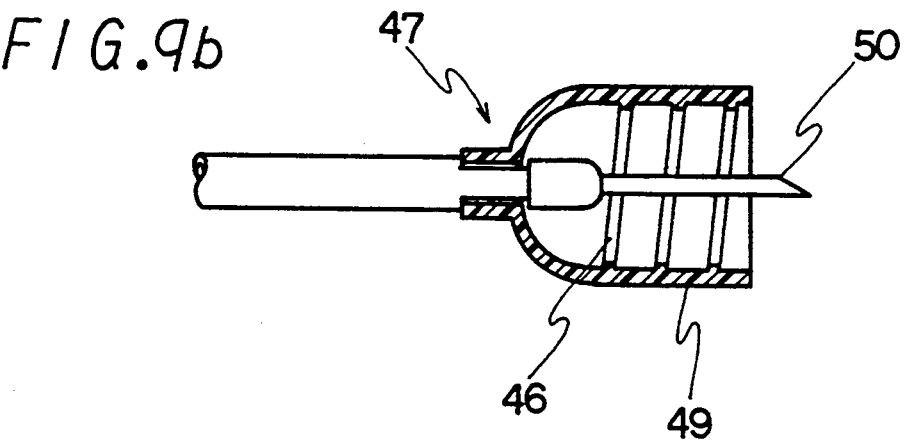
FIG. 9b is a partially longitudinal sectional view of an infusion tube to be connected to the intravenous catheter of FIG. 8.

FIG. 8 is a perspective view of an embodiment of an intravenous catheter of the present invention having a male screw as a connecting means. FIG. 9a is a partially longitudinal sectional view of the catheter of FIG. 8, and FIG. 9b is a partially longitudinal sectional view of an infusion line to be connected to the catheter of FIG. 8.

As shown in FIGS. 8 and 9a, a catheter of the present invention comprises a tubular connector 40 whereto a tube 42 of a small diameter is connected, characterized in that the connector 40 has an injection site 43, and a connecting means 44 is provided on the external wall of the injection site 43 or on the external wall of a tubular portion near the injection site 43. The connector 40 can be airtightly connected to an infusion line 47 shown in FIG. 9b having at its connection end a connecting means 49 of which shape corresponds to that of the connecting means 44 of FIG. 9a. That is, the catheter and the infusion line 47 can be airtightly and securely connected to each other by sticking a needle 50 of the infusion line 47 into a rubber plug 41 of the injection site 43 of the catheter to make the catheter communicate with the infusion line 47 and then by combining both connecting means.

The injection site 43 is used for infusing plural kinds of liquid drug into a patient by adding other liquid drugs from other infusion lines during fluid therapy. The injection site 43 comprises a tubular body having one or more fluid inlet and a fluid outlet. A cap or plug made of rubber-like elastic material is liquidtightly put on at least one fluid inlet. In the case of a cap, it is put on the fluid inlet, while in the case of a plug, it is inserted into the fluid inlet as shown in FIG. 9a. In that case, a means for supporting the cap or rubber plug 41 might be provided to prevent the detachment of the cap or rubber plug 41. In FIG. 9a, the connecting means 44 functions also as a supporting means.

As a material for the cap or plug, the same material as in the cap or plug of the above-mentioned connector can be employed.

The connecting means 44 serves to connect a catheter to a device to be connected (hereafter representatively referred to as infusion line), and the device has a needle at its connection end. The connecting means 44 alone does not function as a connector, but it cooperates with a connecting means 49 formed at the connection end of the infusion line 47 and combines the connector 40 with the infusion line 47. Accordingly the shape of the connecting means 49 at the connection end of the infusion line 47 varies depending on the shape of the connecting means 44. That is, the shape of the connecting means 44 of the catheter and that of the connecting means 49 of the infusion line 47 are supplementary to each other. Such relationship is found in, for example, a male screw 45 in FIG. 9a and a female screw 46 in FIG. 9b.

The connecting means 44 is provided on the external wall of the injection site 43 or on the external wall of a tubular portion near the injection site 43. It is preferable that the connecting means 44 is so provided as to prevent the rotation of the needle in the rubber plug 41 when the connector of the catheter and the infusion line 47 is connected to each other after a needle 10 of the infusion line 47 is sticked into the rubber plug 41 of the injection site 43. Concretely speaking, the male screw 45 is preferably fixed to the connector 40, i.e. adhered to or formed integrally with the connector 40, when the connecting means 4 comprises the male screw 45 (see FIG. 9a). In that case, it is necessary to employ, as a connecting means 49 of the infusion line 47, a rotatable female screw 46 for a fixed male screw 45 (see FIG. 9b).

A tube 42 is a main portion of the catheter. In use, an free end of the tube 42 is remained in vein of a patient. Fluid therapy is carried out by infusing liquid drug and the like into vein through the injection site 43. As material for the tube 42, soft synthetic resin can be employed, and the material is required to have bio-compatibility. Concrete examples of the preferably used material are, for example, vinyl chloride resin, polyurethane, and silicone rubber.

Next a method of using an intravenous catheter of the present invention is explained.

In the case of a catheter shown in FIG. 9a having a male screw 45 as a connecting means 44, a needle 50 of the infusion line 47 having a female screw 46 as a connecting means 49 as shown in FIG. 9b is sticked into a rubber plug 41 of an injection site 43 of the catheter. Then the rotation of the connecting means 49 of the infusion line 47 with one hand in the direction in which the connecting means 49 is screwed, while holding the catheter with other hand, gives the firm connection between the infusion line 47 and the catheter without causing the rotation of the needle 50 in the rubber plug 41.

Finally an infusion tube adapting a connector of the present invention is explained.

Figure 10:
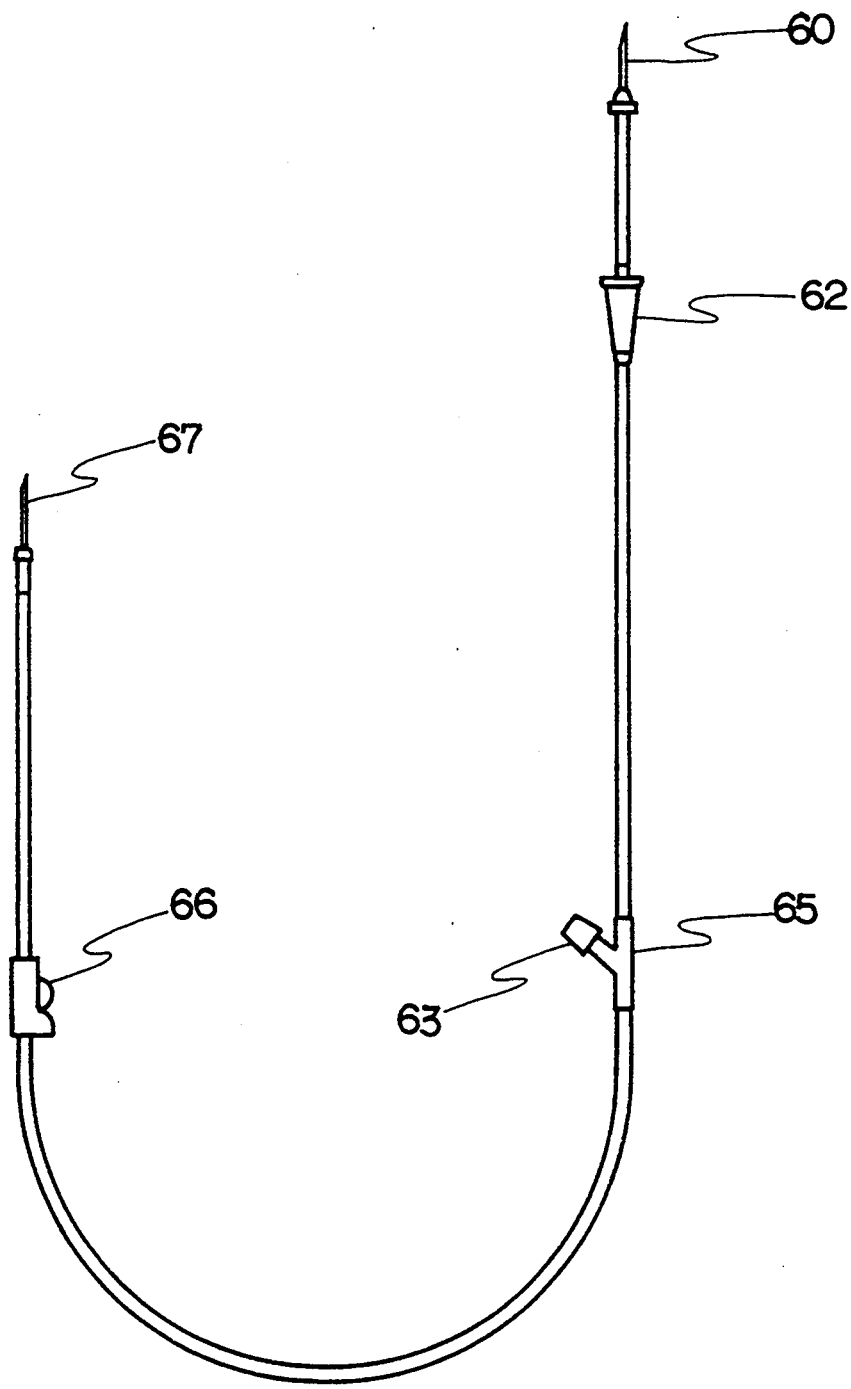
FIG. 10 is a schematic view of an embodiment of an infusion tube of the present invention.
Figure 11:
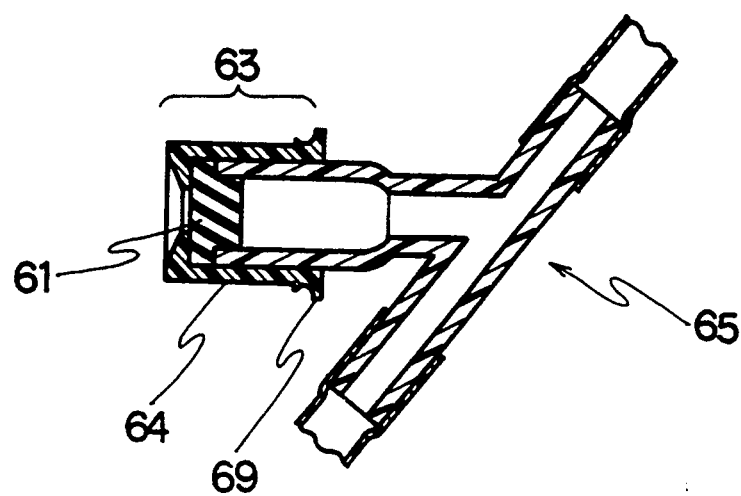
FIG. 11 is a partially longitudinal sectional view of the infusion tube of FIG. 10.

FIG. 10 is a perspective view of an embodiment of an infusion tube of the present invention having a male screw as a connecting means. FIG. 11 is a partially longitudinal sectional view of the infusion tube of FIG. 10, and FIG. 12 is a partially longitudinal sectional view of another embodiment of an infusion tube of the present invention.

Figure 12:
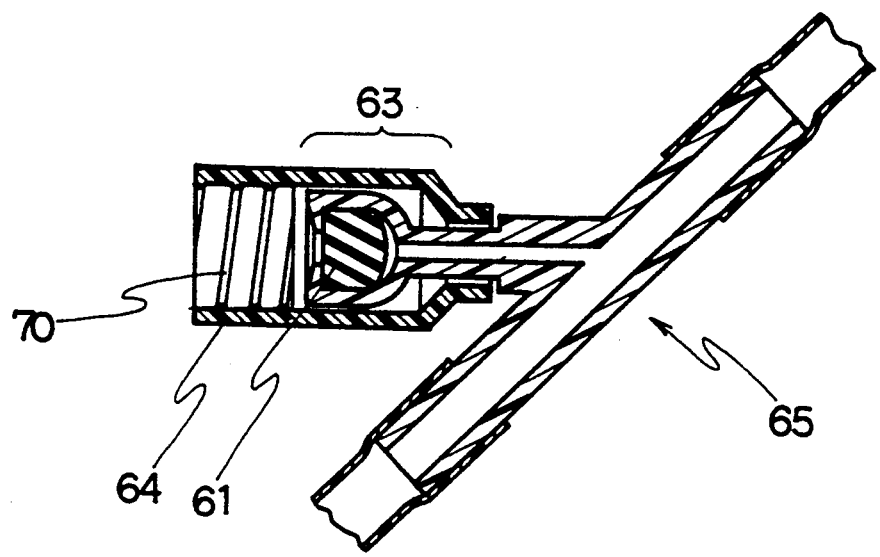
FIG. 12 is a partially longitudinal sectional view of another embodiment of an infusion tube of the present invention.

As shown in FIGS. 10 to 12, an infusion tube of the present invention comprises a spike needle or piercing spike (hereafter referred to as spike) 60, a drip chamber 62, an injection site 63, a flow-controlling means (a roller minicramp 66 is employed in FIG. 10), and an intravenous needle 67, and is characterized in that the injection site 63 is provided at a diverged tube of a tubular body (a Y-shaped tube 65 is employed in FIG. 10), and that a connecting means 64 is provided on the external wall of the injection site 43 or on the external wall of a tubular portion near the injection site 63.

The connecting means 64 can be airtightly connected to an infusion line shown in FIGS. 9b and 3b having at its connection end a connecting means of which shape corresponds to that of the connecting means of FIG. 11 or FIG. 12. That is, in the case of an infusion line of FIG. 9b, the infusion tube and the infusion line 47 can be airtightly and securely connected to each other by sticking a needle 50 of the infusion line 47 into the injection site 63 of the infusion line to make the infusion tube communicate with the infusion line 97 and then by combining both connecting means 64, 49.

The spike 60, drip chamber 62, Y-shaped tube 65 and intravenous needle 67 are connected to one another by means of, for example, a tube made of soft vinyl chloride resin, and constitutes an infusion line. The roller cramp 66 is provided between the Y-shaped tube 65 and intravenous needle 67.

The spike 60 is sticked into a plug of a container such as a bag in order to flow liquid drug and the like in the container into an infusion tube. The drip chamber 62 is used to monitor the priming of liquid drug and the like into the infusion tube and drip rate of liquid drug and the like flown. The Y-shaped tube 65 is a tubular body having a diverged route for introducing liquid drug and the like from other infusion routes. The intravenous needle 67 is sticked into vein of a patient to infuse liquid drug and the like into the vein of the patient.

The injection site 63 is used for infusing plural kinds of liquid drug into a patient by adding other liquid drugs from other infusion lines during fluid therapy. The injection site 63 comprises a tubular body having one or more fluid inlet and a fluid outlet. A cap or plug made of rubber-like elastic material is liquidtightly put on at least one fluid inlet. In the case of a cap, it is put on the diverged route, while in the case of a plug, it is inserted into the diverged route. In that case, a means for supporting the cap or rubber plug 61 might be provided to prevent the detachment of the cap or rubber plug 61. In FIG. 11, the connecting means 64 functions also as a supporting means.

As a material for the cap or plug, the same material as in the cap or plug of the above-mentioned connector can be employed.

The connecting means 64 serves to connect an infusion tube to an infusion line having a needle at its connection end.

The connecting means 64 alone does not function as a connector, but it cooperates with a connecting means 49 formed at the connection end of the infusion line and combines the infusion tube with the infusion line. Accordingly the shape of the connecting means at the connection end of the infusion line varies depending on the shape of the connecting means 44. That is, the shape of the connecting means 44 of the infusion tube and that of the connecting means 49 of the infusion line 8 are supplementary to each other. Such relationship is found in, for example, a male screw 69 in FIG. 11 and a female screw 46 in FIG. 9b, or a female screw 70 in FIG. 12 and a male screw 13 in FIG. 3b. The connecting means 64 is provided on the external wall of the injection site 63 or on the external wall of a tubular portion near the injection site 63. It is preferable that the connecting means 64 is so provided as to prevent the rotation of the needle in the rubber plug 61 when the infusion tube and the infusion line is connected to each other after a needle of the infusion line 47 is sticked into the rubber plug 61 of the injection site 63. Concretely speaking, the male screw 69 is preferably fixed to the injection site 63 or the diverged route near the injection site 63, when the connecting means 64 comprises the male screw 69 (see FIG. 11). In that case, it is necessary to employ, as a connecting means 49 of an infusion line 47, a rotatable female screw 46 for a fixed male screw 69 of the infusion tube (see FIG. 9b), and a fixed male screw 13 for a rotatable female screw 70 of the infusion tube (see FIG. 3b).

As a tubular body having a diverged route, various kinds of tubular bodies such as T-shaped tube, crossed tube and tube having a plurality of diverged routes are employable beside the Y-shaped tube 65. Among them, a Y-shaped tube or T-shaped tube is generally employed.

Next a method of using infusion tube of the present invention is explained.

In the case of a infusion tube shown in FIG. 11 having a male screw 69 as a connecting means 64, a needle 50 of the infusion line 47 having a female screw 46 as a connecting means 49 as shown in FIG. 9b is sticked into a rubber plug 61 of an injection site 63 of the infusion tube. Then the rotation of the connecting means 49 of the infusion line 47 with one hand in the direction in which the connecting means 49 is screwed, while holding the infusion tube with other hand, gives the firm connection between the infusion line 47 and the infusion tube without causing the rotation of the needle 50 in the rubber plug 61.

The connector of the present invention is applicable to other devices such as blood circuit and solution infusion device besides an infusion needle, intravenous catheter and infusion tube explained hereinbefore. Though male screws and female screws are employed in the above explanations for an injection needle, intravenous catheter and infusion tube, pin-shaped or stake-shaped projections are off course employable.

As is clear from the above explanation, the following effects can be obtained by the use of a connector of the present invention.

(1) Sheets or clothes of a patient is not soiled with liquid drug since the needle of an infusion line is not pulled out during treatment.

(2) Infection by the air through an injection site can be perfectly avoided by the structure enabling airtight connection.

What is claimed is:

1. A connector assembly including an injection needle for providing fluid communication through a closed injection site at one end of an infusion line for infusing fluid therapy to a patient which consists of:
 a tubular member having first and second ends, a through passage, and a reduced external diameter portion between said first and second ends,
 an injection needle having one end fitted to said first end of said tubular member and having an internal fluid passage,
 a tube connected to said second end of said tubular member,
 a connector having one end mounted for rotation around said reduced diameter portion of said tubular member,
 an infusion line,
 a complimentary connector having a closed injection site at one end of said infusion line,
 connecting means on said connector for securing said connector to said complimentary connector, and
 a second end of said needle extending beyond said connecting means to permit said needle to pierce said injection site prior to engagement of said connecting means with said complimentary connector whereby said connector and said complimentary connector are connected together subsequent to piercing said needle through said injection site.

2. A connector assembly including an injection needle as defined by claim 1, wherein said first end of said tubular member is formed as a hub for rotatably mounting connector between said hub and said tube.

3. A connector assembly including an injection needle as defined by claim 1, wherein said connecting means is a thread provided internally of said connector.

4. A connector assembly including an injection needle for providing fluid communication through a closed injection site at one end of an infusion line for infusing fluid therapy to a patient which consists of:
 a tubular member having first and second ends, a through passage, and a reduced external diameter portion between said first and second ends,
 an injection needle having one end fitted to said first end of said tubular member and having an internal fluid passage,
 a tube, said tube being slidably received by said second end of said tubular member to establish fluid communication therethrough,
 a connector having one end mounted for rotation around said reduced diameter portion of said tubular member,
 an infusion line,
 a complementary connector having a closed injection site at one end of said infusion line,
 connecting means on said connector for securing said connector to said complementary connector, and
 a second end of said needle extending beyond said connecting means to permit said needle to pierce said injection site prior to engagement of said connecting means with said complementary connector whereby said connector and said complementary connector are connected together subsequent to piercing said needle through said injection site.

5. A connector assembly including an injection needle as defined by claim 4, wherein said first end of said tubular member is formed as a hub for rotatably mounting said connector between said hub and said tube.

6. A connector assembly including an injection needle as defined by claim 4, wherein said connecting means is a thread provided internally of said connector.

* * * * *